(12) United States Patent
Kawanishi et al.

(10) Patent No.: US 6,905,464 B2
(45) Date of Patent: Jun. 14, 2005

(54) VISCERAL FAT METER PROVIDED WITH TONOMETER

(75) Inventors: Shozo Kawanishi, Hyogo (JP); Koichi Okita, Hyogo (JP)

(73) Assignee: Yamato Scale Co., Ltd., Akashi (JP)

( * ) Notice: Subject to any disclaimer, the term of this patent is extended or adjusted under 35 U.S.C. 154(b) by 0 days.

(21) Appl. No.: 10/470,744

(22) PCT Filed: Feb. 1, 2002

(86) PCT No.: PCT/JP02/00861

§ 371 (c)(1),
(2), (4) Date: Aug. 11, 2003

(87) PCT Pub. No.: WO02/067777

PCT Pub. Date: Sep. 6, 2002

(65) Prior Publication Data

US 2004/0077955 A1 Apr. 22, 2004

(30) Foreign Application Priority Data

Feb. 23, 2001 (JP) ........................................ 2001-048940

(51) Int. Cl.[7] ................................................ A61B 5/00
(52) U.S. Cl. ...................... 600/301; 600/485; 600/490; 600/547
(58) Field of Search ................................ 600/300, 301, 600/485–507, 547

(56) References Cited

U.S. PATENT DOCUMENTS

| | | | | |
|---|---|---|---|---|
| 5,579,782 A | * | 12/1996 | Masuo | 600/547 |
| 5,680,869 A | * | 10/1997 | Ogura | 600/485 |
| 6,327,495 B1 | * | 12/2001 | Iwabuchi et al. | 600/547 |
| 6,336,136 B1 | * | 1/2002 | Harris | 709/219 |
| 6,354,996 B1 | * | 3/2002 | Drinan et al. | 600/300 |
| 6,516,221 B1 | * | 2/2003 | Hirouchi et al. | 600/547 |
| 6,643,542 B1 | * | 11/2003 | Kawanishi | 600/547 |
| 6,752,760 B2 | * | 6/2004 | Kouou | 600/547 |
| 2002/0151815 A1 | * | 10/2002 | Kawanishi et al. | 600/547 |
| 2003/0158501 A1 | * | 8/2003 | Uchida et al. | 600/587 |

FOREIGN PATENT DOCUMENTS

| | | | |
|---|---|---|---|
| JP | 7-39535 | 2/1995 | |
| JP | 07-039535 | * 10/1995 | ............ A61B/5/05 |
| JP | 10-192258 | 7/1998 | |
| JP | 11-76187 | 3/1999 | |
| JP | 2000-237149 | 9/2000 | |
| JP | 2000-350710 | 12/2000 | |

* cited by examiner

*Primary Examiner*—Robert L. Nasser
*Assistant Examiner*—Patricia C. Mallari
(74) *Attorney, Agent, or Firm*—Armstrong, Kratz, Quintos, Hanson & Brooks, LLP (57) ABSTRACT

A visceral fat scale equipped with a sphygmomanometer is described, with which a subject can keep track of blood pressure values and grasp the state of obesity to attain more accurate, comprehensive and diversified diagnoses and disease prevention. The visceral fat scale is designed such that after exerting pressure to an artery of a subject by inflation of a cuff, a pulse wave signal is detected in the course of gradual cuff deflation and blood pressure is obtained based on the detected pulse wave signal. The scale comprises an increment/decrement key and display mode selector key for inputting personal data of the subject; an arithmetic operation unit for calculating the amount of visceral fat of the subject based on data input by these keys; and a display unit for displaying a result of the calculation performed by the arithmetic operation unit.

15 Claims, 9 Drawing Sheets

VISCERAL FAT METER PROVIDED WITH TONOMETER

TECHNICAL FIELD

The present invention relates to a visceral fat scale equipped with a sphygmomanometer, which is capable of making simultaneous measurements of blood pressure and percent body fat.

BACKGROUND ART

The latest studies have thrown considerable light upon the relationship between hypertension and various diseases. People, who are generally diagnosed as having hypertension, with a systolic blood pressure of 140 mmHg or more and a diastolic blood pressure of 90 mmHg or more, commonly develop cerebral hemorrhage and cerebral infarction. In view of this, the importance of health care has been further emphasized in order to prevent diseases caused by high blood pressure. For effective prevention of hypertension, not only periodic medical check-ups such as blood pressure taking but also awareness of the condition of blood pressure on a daily basis become necessary.

Recently, simplified sphygmomanometers which enable easy measurements of blood pressure on a daily basis are commercially available so that continuous, easy personal blood pressure control becomes possible. For such simplified sphygmomanometers, the so-called oscillometric method (pressure pulse wave oscillation method) is prevailing which is distinguished from the Korotcoff method that has been conventionally used as the stethoscopy in the medical field and others. The oscillometric method is carried out in such a manner that a cuff (arm wrap) is worn around fingers, a wrist or an upper arm; air is sent to the cuff to press an artery; pressure in the cuff is gradually released to detect pulse wave components with a pressure sensor; and blood pressure (systolic and diastolic blood pressures) is measured based on the detected pulse wave components.

A known electronic sphygmomanometer utilizing the oscillometric method is designed as follows: For setting of a target inflation value for the cuff, a cuff pressure signal is detected, for example, during inflation of the cuff. Then, a systolic blood pressure (e.g., a cuff pressure corresponding to one-half the maximum amplitude of the pulse wave) is simply estimated from the maximum amplitude value of the pulse wave included in the signal, and a value obtained by adding a specified value to the estimated systolic blood pressure is automatically set as a target inflation value. In this case, for the purpose of reducing the time required for a blood pressure measurement as well as the pain given to the person under measurement, the rising speed of pressure at the time of cuff inflation is set to a higher value than the speed of cuff deflation during which a measurement of systolic and diastolic pressures is made.

In the medical field, there have recently been advances in the studies of the association between hypertension and obesity and it has been found that obesity is not simply a state of overweight and the distribution of body fat bears relevance to blood pressure. It has been further reported that the distribution of abdominal body fat (visceral fat type obesity) deeply concerns hypertension.

In addition to BMI (Body Mass Index=body weight/(body height)$^2$) that is widely used as an index indicative of the degree of obesity, various indices (e.g., percent body fat, the cross-sectional area of abdominal visceral fat, etc.) to an assessment of visceral fat type obesity have been devised and respectively proved to be useful in the clinical sites. Of these indices, percent body fat is obtained based on personal specific data on the subject such as height, weight, age and sex and based on the measurement of body impedance. The cross sectional area of abdominal visceral fat is obtained from a CT scan of the abdomen of the subject around his umbilicus and from estimation based on data on the waist size of the subject obtained by measuring the abdomen of the subject around his umbilicus as well as the personal specific data described above.

The above-described conventional sphygmomanometer has, however, revealed such a drawback that since it measures and deals with blood pressure alone, it cannot provide more accurate diagnosis of hypertension taking account of the relationship with the aforesaid visceral fat type obesity.

In addition, the conventional sphygmomanometer of this type presents another problem when setting a target inflation value for the cuff. Specifically, since the conventional sphygmomanometer is susceptible to the influence of noise caused by the fluctuation of a cuff pressure signal occurring just after cuff inflation, the detection of a pulse wave at the time of cuff inflation cannot be always carried out correctly, so that an estimated value of systolic blood pressure and, in consequence, a target inflation value based on the estimated value become wrong. Especially, if the target inflation value is set to an abnormally low value, there will occur an error in the later measurement of blood pressure values (i.e., systolic blood pressure and diastolic blood pressure) at the time of cuff deflation due to a lack of inflation.

The present invention has been directed to overcoming the foregoing shortcomings and a primary object of the invention is therefore to provide a visceral fat scale equipped with a sphygmomanometer with which a subject can keep track of his blood pressure values and grasp the state of obesity to realize more accurate, comprehensive and diversified diagnoses and disease prevention. Another object of the invention is to provide a visceral fat scale equipped with a sphygmomanometer wherein even if it fails in making an accurate measurement of the maximum amplitude value of a pulse wave at the time of cuff inflation, an error will not occur in the measurement of blood pressure values at the time of cuff deflation.

DISCLOSURE OF THE INVENTION

The above objects can be accomplished by a visceral fat scale equipped with a sphygmomanometer according to a first aspect of the invention, wherein after exerting pressure to an artery of a subject by inflation of a cuff, a pulse wave signal is detected in the course of gradual cuff deflation and blood pressure is obtained based on the detected pulse wave signal, the visceral fat scale comprising:

an input device for inputting personal data of the subject;

an arithmetic operation unit for calculating the amount of visceral fat of the subject based on the data input by the input device; and a display unit for displaying a result of the calculation performed by the arithmetic operation unit.

According to the invention, since the amount of visceral fat of a subject is calculated by the arithmetic operation unit based on personal data input by the input device and the result of the calculation is displayed on the display unit, the subject can keep track of his blood pressure values and grasp the amount of visceral fat, in other words, the state of obesity, so that control of blood pressure in connection with visceral fat type obesity becomes possible. This enables more accurate, comprehensive, diversified diagnoses and disease prevention with a simplified device, compared to the conventional health management based on blood pressure alone.

Preferably, in the invention, the personal data input by the input device includes the height, weight and waist size of the subject, and the arithmetic operation unit calculates the BMI of the subject in addition to the amount of visceral fat of the subject based on the data input by the input device. This makes it possible to calculate not only the amount of visceral fat but also BMI (Body Mass Index) that is internationally used as an index to an assessment of obesity/emaciation, so that more reliable data on the state of obesity can be attained.

In this case, the display unit preferably displays the ranks of the visceral fat amount and BMI of the subject, these indices respectively having a plurality of ranks. By representing the degree of obesity according to the ranks of the indices, the subject can more easily make a self assessment of the degree of obesity.

Preferably, the arithmetic operation unit makes an assessment of obesity by comparing the visceral fat amount and BMI of the subject with their respective reference values for assessment which have been input beforehand, and wherein the display unit displays a result of the assessment of obesity.

The display unit preferably displays blood pressure values and the amount of visceral fat at the same time. This allows the subject to grasp his blood pressure values and the state of obesity on a first viewing of the display unit.

In addition, it is preferable that the arithmetic operation unit calculate the amount of change from a previous measurement result and the ratio of the present measurement result to the previous measurement result for the blood pressure values and visceral fat amount of the subject, and that the display unit display a result of the calculation. With this arrangement, the subject can more accurately grasp his state of health through the relationship between the degree of change in his blood pressure and the degree of change in the amount of visceral fat of his own, so that he can utilize the acquisition for proper health care and disease prevention.

The amount of visceral fat may be the cross-sectional area of abdominal visceral fat of the subject which is used as an index to an assessment of obesity in the clinical site. Herein, the target cuff inflation value may be determined by a systolic blood pressure estimated based on a pulse wave generated during cuff inflation and by the cross-sectional area of abdominal visceral fat. Alternatively, the target cuff inflation value may be determined by a systolic blood pressure estimated based on a pulse wave generated during cuff inflation and by a result of an assessment of obesity. With this arrangement, even if the maximum amplitude value of a pulse wave generated during cuff inflation cannot be correctly measured, there will not occur such an unfavorable situation that blood pressure values (systolic blood pressure and diastolic blood pressure) to be measured at the time of cuff deflation become incorrect owing to a lack of inflation.

According to a second aspect of the invention, there is provided a visceral fat scale equipped with a sphygmomanometer, wherein after exerting pressure to an artery of a subject by inflation of a cuff, a pulse wave signal is detected in the course of gradual cuff deflation and blood pressure is obtained based on the detected pulse wave signal, the visceral fat scale comprising:

an input device for inputting personal data including the height, weight and waist size of the subject;

electrodes for current application and electrodes for measurement which are brought into contact with part of the body of the subject;

a body impedance measuring unit for measuring the body impedance of the subject based on a signal from the measurement electrodes;

an arithmetic operation unit for calculating at least any of the BMI, percent body fat and visceral fat amount of the subject based on data input by the body impedance measuring unit and data input by the input device; and a display unit for displaying a result of the calculation performed by the arithmetic operation unit.

In addition to the first aspect, the invention has the feature that the body impedance of the subject is measured and, based on this measurement, the percent body fat of the subject is calculated and displayed. Therefore, the subject can more accurately grasp not only his blood pressure values but also the state of obesity and, accordingly, the effect of the first aspect is enhanced.

Preferably, in the invention, the display unit displays the rank of any of the BMI, percent body fat and visceral fat amount of the subject, each of these indices having a plurality of ranks. With this arrangement, the subject can more easily make an assessment of the degree of obesity of his own.

Preferably, the arithmetic operation unit makes an assessment of obesity by comparing any of the BMI, percent body fat and visceral fat amount of the subject with their respective values for assessment which have been input beforehand, and the display unit displays a result of the assessment of obesity.

The display unit preferably displays blood pressure values and the amount of visceral fat at the same time. This allows the subject to grasp his blood pressure values and the state of obesity on a first viewing of the display unit.

In addition, it is preferable that the arithmetic operation unit calculate the amount of change from a previous measurement result and the ratio of the present measurement result to the previous measurement result for the blood pressure values and visceral fat amount of the subject, and that the display unit display a result of the calculation.

The amount of visceral fat may be the cross-sectional area of abdominal visceral fat of the subject which is used as an index to an assessment of obesity in the clinical site. Herein, the target cuff inflation value may be determined by a systolic blood pressure estimated based on a pulse wave generated during cuff inflation and by the cross-sectional area of abdominal visceral fat. Alternatively, the target cuff inflation value may be determined by a systolic blood pressure estimated based on a pulse wave generated during cuff inflation and by a result of the assessment of obesity.

BEST MODE FOR CARRYING OUT THE INVENTION

Referring now to the accompanying drawings, there will be described preferred embodiments of a visceral fat scale equipped with a sphygmomanometer according to the invention.

Figure 1:
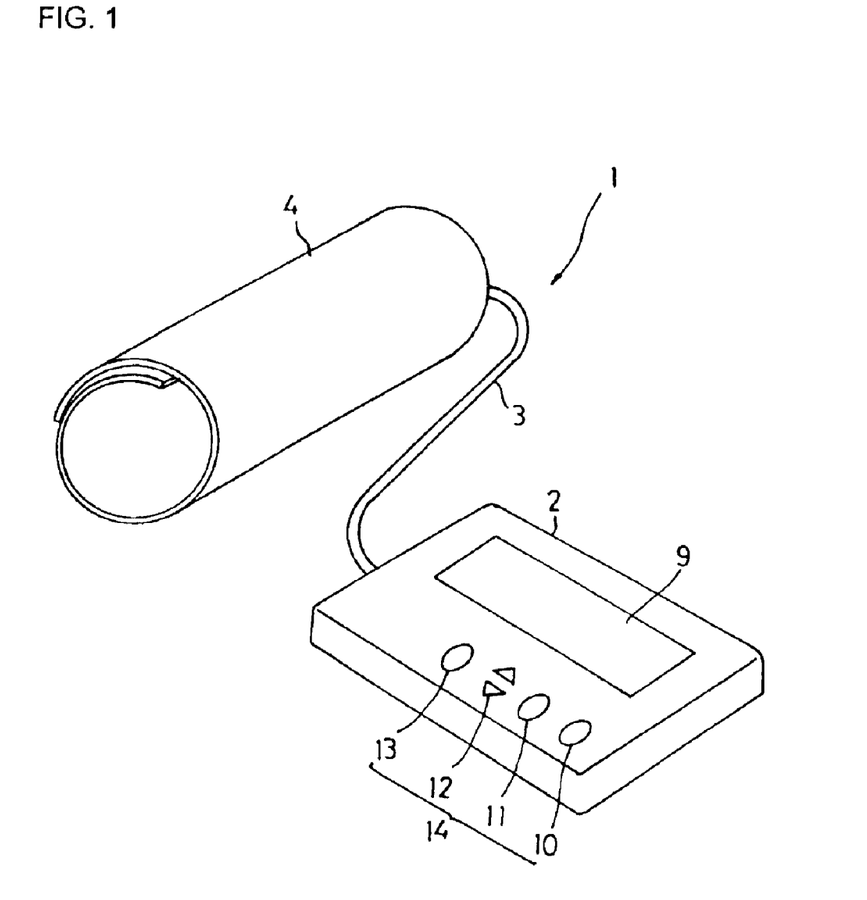
FIG. 1 is a general perspective view of a visceral fat scale equipped with a sphygmomanometer according to a first embodiment of the invention.
Figure 2:
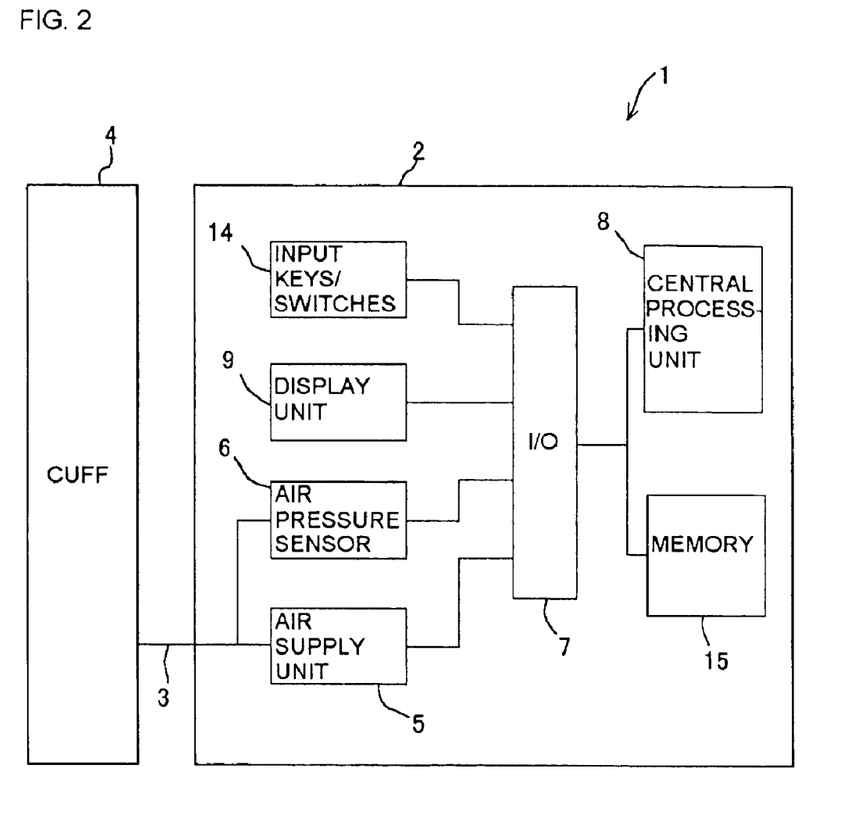
FIG. 2 is a block diagram of the visceral fat scale equipped with a sphygmomanometer according to the first embodiment.

FIGS. 1 and 2 show a general perspective view and block diagram, respectively, of a visceral fat scale equipped with a sphygmomanometer according to a first embodiment of the invention.

The visceral fat scale equipped with a sphygmomanometer 1 of this embodiment is designed to measure blood pressure, using the so-called oscillometric blood pressure measuring method (the pressure pulse wave oscillation method) and has as main components, a machine body 2 and a cuff (arm wrap) 4 which is connected to the machine body 2 through an air tube 3 and wearable around an arm of a subject. Disposed within the machine body 2 is an air supply unit 5 which is connected to the air tube 3 and comprised of a pump for supplying the cuff 4 with air and a pressure release valve for releasing the air pressure of the cuff 4, and others. An air pressure sensor 6 is also disposed within the machine body 2, for detecting pulse wave components through detection of the air pressure of the cuff 4. The air supply unit 5 and the air pressure sensor 6 are connected to a central processing unit (arithmetic operation unit) 8 through an I/O circuit 7.

The machine body 2 has, at its top face thereof, a display unit 9 and input keys/switches 14 which are comprised of a power switch 10, a blood pressure measurement starting switch 11, an increment/decrement key 12, and a display mode selector key 13. Further, the central processing unit 8 is provided with a memory 15 for storing data such as personal data which has been input by the input keys/switches 14 and sent to the memory 15 through the I/O circuit 7. It should be noted that the increment/decrement key 12 and the display mode selector key 13 correspond to the input device of the present invention.

Figure 3:
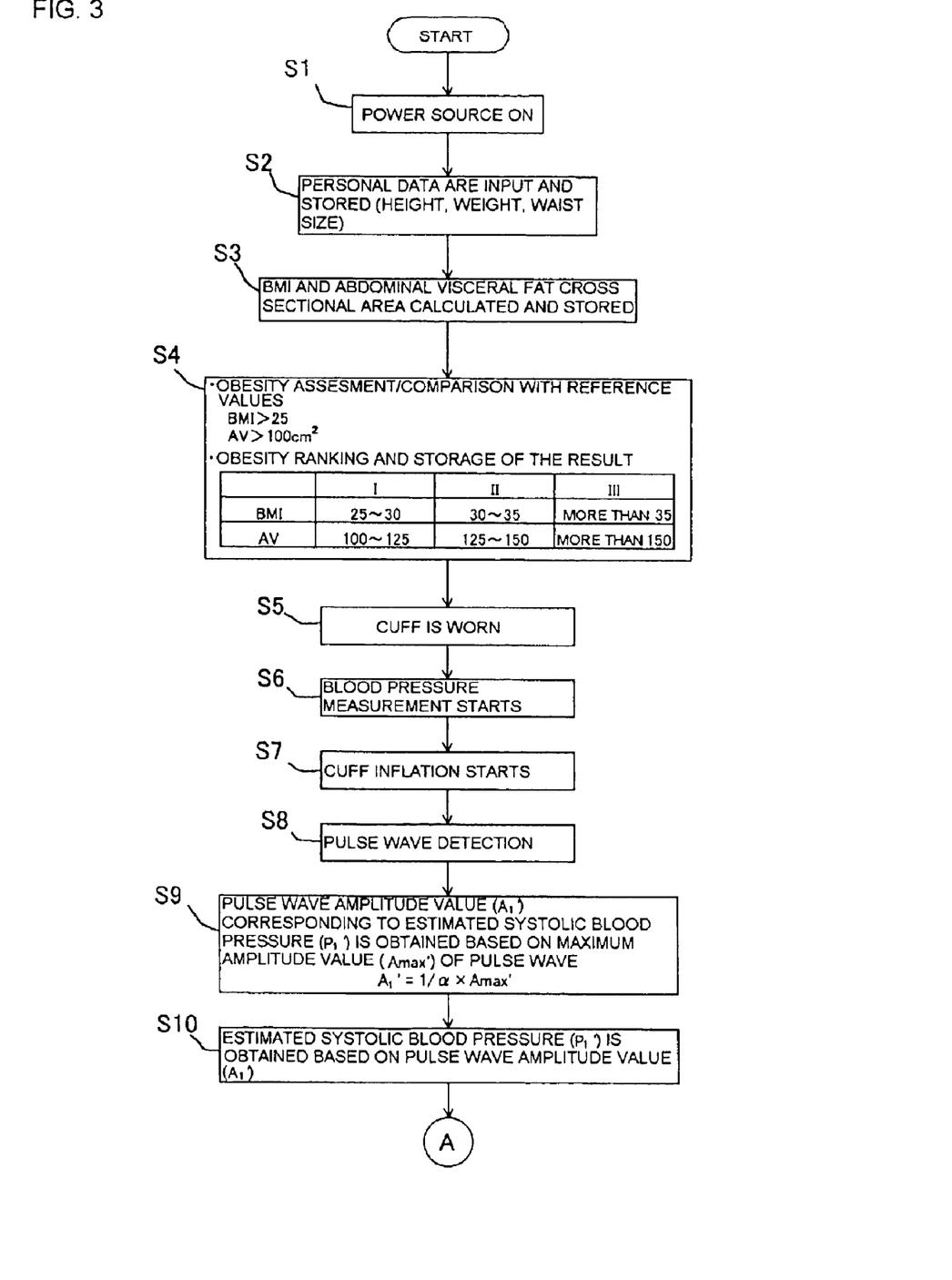
FIG. 3 is a flow chart (the first stage) of the operation of the visceral fat scale equipped with a sphygmomanometer according to the first embodiment.
Figure 4:
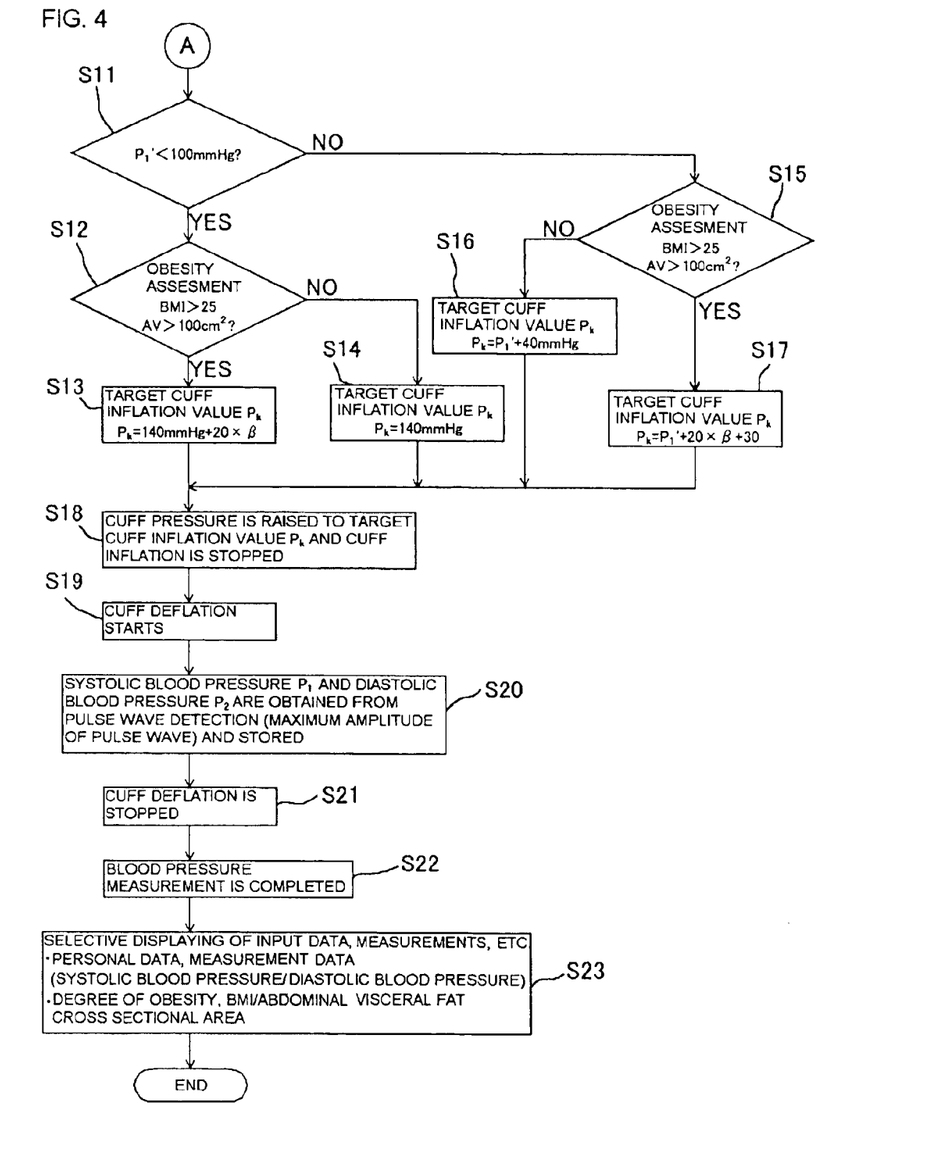
FIG. 4 is a flow chart (the second stage) of the operation of the visceral fat scale equipped with a sphygmomanometer according to the first embodiment.

Reference is made to the flow charts of FIGS. 3 and 4 to describe the operation of the visceral fat scale equipped with a sphygmomanometer 1 having the above structure. Note that code S stands for a step.

S1: The power switch 10 is turned ON to put the machine body 2 into operation.

S2: The display mode selector key 13 and the increment/decrement key 12 are operated thereby selectively inputting the personal data of the subject such as height, weight and waist size. The data thus input is stored in the memory 15.

S3: Based on the personal data stored in the memory 15, the central processing unit 8 calculates the BMI and abdominal visceral fat cross-sectional area (AV) of the subject and the results of the calculations are stored in the memory 15. The arithmetic expressions used for the above calculations have been stored in the memory 15 beforehand and are called into the central processing unit 8 when executing the arithmetic operations. As the simplest expression for obtaining abdominal visceral fat cross-sectional area (AV), the following regression equation (1) is used:

$$AV = a_1 \times W_L + d_1 \qquad (1)$$

where $W_L$ is waist size. The coefficient $a_1$ and constant $d_1$ of this expression are derived from a statistic technique such as regression analysis, based on the correlation between the waist size and abdominal cross-section C/T data of a selected group of subjects.

S4: The BMI and abdominal visceral fat cross-sectional area (AV) which have been calculated and stored in the memory 15 at step S3 are compared to their reference values set for the obesity assessment. The rank of obesity for the subject is determined and stored in the memory 15. The reference values and arithmetic expression used for the comparison have been stored in the memory 15 and are called into the central processing unit 8 when executing the arithmetic operations. As the reference values for the obesity assessment, BMI=25 (for male and female) and abdominal visceral fat cross-sectional area (AV)=100 cm² (for male and female) are used. It should be noted that BMI is internationally used as an index to an assessment of obesity/emaciation and abdominal visceral fat cross-sectional area (AV) represents the amount of distributed visceral fat and is used for diagnoses of obesity in the clinical site. Obesity is ranked according to these indices BMI and AV. More concretely, BMI is classified as follows: the range of 25 to 30 is rank I, the range of 30 to 35 is rank II and the range of more than 35 is rank III. Abdominal visceral fat cross-sectional area (AV) is classified as follows: the range of 100 to 125 cm² is rank I, the range of 125 to 150 cm² is rank II and the range of more than 150 cm² is rank III.

S5: Subsequently, the cuff 4 is worn around an arm of the subject for blood pressure measurement.

S6: The blood pressure measurement starting switch 11 is depressed, thereby starting blood pressure measurement.

S7: The air supply unit 5 supplies the cuff 4 with air so that the cuff 4 is inflated.

Figure 5:
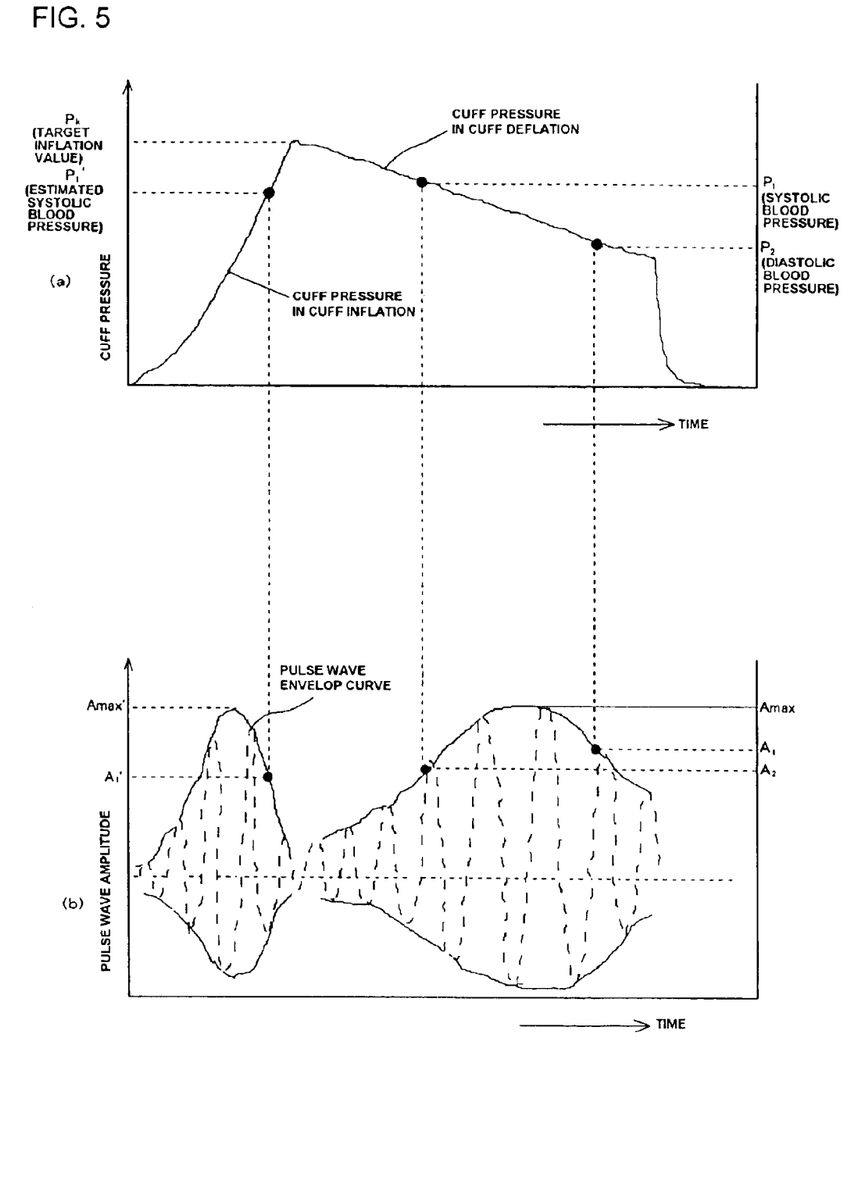
FIGS. 5(a) and 5(b) are explanatory graphs showing a blood pressure measuring method according to the first embodiment.

S8: The pressure of the cuff 4 is detected by the air pressure sensor 6 while the cuff 4 being inflated and a pulse wave to be superimposed on a pressure signal is detected in the course of the inflation of the cuff 4. The maximum value Amax' of the amplitude of the pulse wave is obtained to be stored in the memory 15 (See FIG. 5).

S9: To estimate a systolic blood pressure $P_1'$ from the maximum amplitude value Amax' of the pulse wave, an amplitude value $A_1'$, for example, is obtained which is one α-th (1/α) the maximum amplitude value Amax' of the pulse wave, in other words, which is derived from the following equation:

$$A1' = 1/\alpha \times A\text{max}' \qquad (2)$$

S10: Then, the cuff pressure (estimated systolic blood pressure) $P_1'$ corresponding to the amplitude value $A_1'$ obtained at step S9 is obtained and stored in the memory 15.

S11: To determine a target cuff inflation value based on the estimated systolic blood pressure $P_1'$, the estimated systolic blood pressure $P_1'$ is compared to a specified value (which is, herein, 100 mmHg).

S12: If the estimated systolic blood pressure $P_1'$ is less than 100 mmHg, a check is made to determine whether or not each index (BMI and AV) exceeds its reference value, in other words, whether BMI>25 and AV>100 cm² hold. This check is made in order to determine a target cuff inflation value $P_k$ as security for errors in the measurement and estimation, based on the result of the assessment of obesity with the stored obesity indices (BMI and AV).

S13: If obesity is diagnosed based on the judgement with the indices (BMI and AV), in other words, if BMI>25 and AV>100 cm² hold, the target cuff inflation value $P_k$ is determined from the equation (3):

$$Pk = 140 \text{ mmHg} + 20 \times \beta \qquad (3)$$

where β represents a value looked up in Table 1 with an obesity rank I, II or III.

TABLE 1

| OBESITY RANK | I | II | III |
|---|---|---|---|
| BMI | β = 1 | β = 1.5 | β = 2 |
| AV | β = 1 | β = 2 | β = 3 |

Since the determining factor for the target cuff inflation value $P_k$ thus takes account of the result of the obesity assessment, there will not occur such an undesirable situation that blood pressure values (i.e., systolic blood pressure and diastolic blood pressure) are incorrectly measured during later cuff deflation, even if the measurement of the maximum amplitude value Amax' of the pulse wave generated during cuff inflation is not correctly made owing to insufficient inflation.

S14: If at least either index BMI or AV does not indicate obesity in the judgement of Step S12, the target cuff inflation value $P_k$ is determined by the following equation (4):

$$Pk = 140 \text{ mmHg} \tag{4}$$

In this way, the estimated systolic blood pressure $P_1'$ is compared to the specified value (100 mmHg) based on the measurement of the maximum amplitude value Amax' of the pulse wave generated during cuff inflation, and if it is determined that the estimated value $P_1'$ is less than the specified value and obesity is not diagnosed in the obesity assessment, the target cuff inflation value $P_k$ is set to the lowest limit value (e.g., 140 mmHg). With this arrangement, if an error occurs in the measurement of the maximum amplitude value Amax' and in the calculation of the estimated systolic blood pressure $P_1'$, the target cuff inflation value $P_k$ will be set to its lowest limit value so that occurrence of an undesirable situation can be avoided in which the measurement of blood pressure values (i.e., systolic blood pressure and diastolic blood pressure) is incorrectly made during later cuff deflation.

S15: If it is judged at step S11 that the estimated systolic blood pressure $P_1'$ is 100 mmHg or more, a check is then made similarly to the step S12 to determine whether each of the indices (BMI and AV) exceeds its reference value for the obesity assessment, in other words, whether BMI>25 and AV>100 cm$^2$ hold.

S16: If at least either of the indices BMI and AV does not indicate obesity, the target cuff inflation value $P_k$ is determined by the following equation (5):

$$P_k = P_1' + 40 \text{ mmHg} \tag{5}$$

S17: On the other hand, if both indices BMI and AV indicate obesity, in other words, if BMI>25 and AV>100 cm$^2$ hold, the target cuff inflation value $P_k$ is determined by the following equation (6):

$$P_k = P_1' + 20 \times \beta + 30 \tag{6}$$

S18: After the target cuff inflation value $P_k$ has been determined in the above-described manner, cuff inflation is carried out until the cuff pressure reaches the target cuff inflation value $P_k$ and then stopped.

S19: After it is judged that the cuff inflation has stopped, the valve of the air supply unit 5 is switched to the evacuation side so that extremely slow deflation of the cuff 4 starts.

S20: A pulse wave to be superimposed on a pressure signal in the cuff deflation phase is detected and the maximum amplitude value Amax of the pulse wave is obtained and stored. Then, in order to estimate a systolic blood pressure $P_1$ from the maximum amplitude value Amax of the pulse wave, an amplitude value $A_1$ which is one α-th (1/α) the maximum amplitude value Amax' of the pulse wave, for example, is obtained, in other words, the amplitude value $A_1$ is obtained from the following equation (7):

$$A1 = 1/\alpha \times A\max \tag{7}$$

To estimate a diastolic blood pressure $P_2$ from the maximum amplitude Amax of the pulse wave, an amplitude value $A_2$ which is one γ-th (1/γ) the maximum amplitude value Amax' of the pulse wave, for example, is obtained, in other words, the amplitude value $A_2$ is obtained from the following equation (8):

$$A1 = 1/\gamma \times A\max \tag{8}$$

The value of 1/α may be 0.5, whereas the value of 1/γ may be 0.7. In place of 1/α and 1/γ, an estimate equation or the like which provides more improved estimation accuracy may be used.

S21: After completion of the measurement of systolic blood pressure and diastolic blood pressure, the evacuation of the cuff 4 is done by rapid deflation within a short time and then, the deflation of the cuff 4 is stopped.

S22: The blood pressure measurement is completed.

S23: After completion of the measurement, the display unit 9 performs selective displaying of the input data such as the personal data (height, weight, sex, age, waist size), the blood pressure measurements (systolic blood pressure and diastolic blood pressure), the indices (BMI and abdominal visceral cross-sectional area) used for the obesity assessment, the result of the assessment, and the degree of obesity (the rank of each index).

The visceral fat scale equipped with a sphygmomanometer 1 of this embodiment may be designed such that data on blood pressure measurements, BMI and abdominal visceral cross-sectional area is stored each time a measurement is made and each data piece is displayed with the amount of change from the result of the previous measurement. In addition, the scale 1 may display the ratio of the present measurement result to the previous measurement result (or the ratio of the change between the present and previous measurement results to the previous measurement result) in terms of blood pressure values and abdominal visceral cross-sectional area. This makes it possible to get an idea of the relationship between the amount of change and the aforesaid ratio with respect to the amount of distributed abdominal visceral fat and blood pressure values, and therefore, health condition can be more accurately grasped based on these values to achieve more adequate health control. Additionally, changes in each data item may be recorded according to a systematic schedule of blood pressure measurements, thereby observing the long-term transition of data and making use of it as a guideline for diagnosis.

Figure 6:
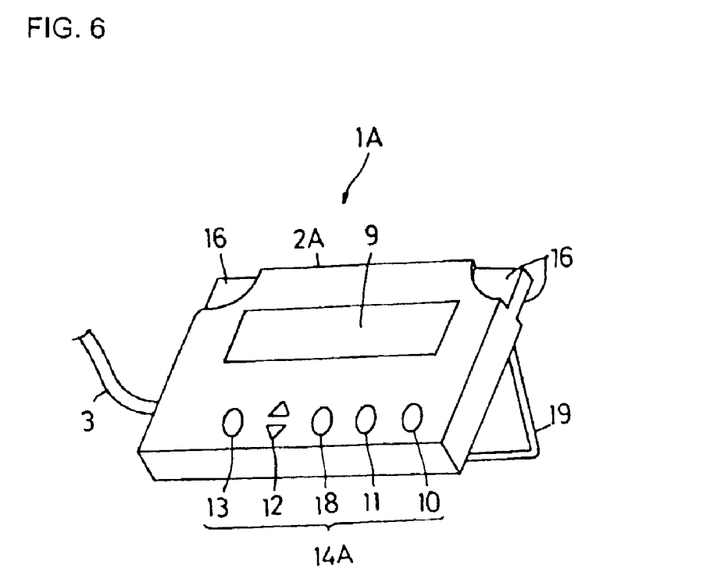
FIG. 6 is a general perspective view of a visceral fat scale equipped with a sphygmomanometer according to a second embodiment.
Figure 7:
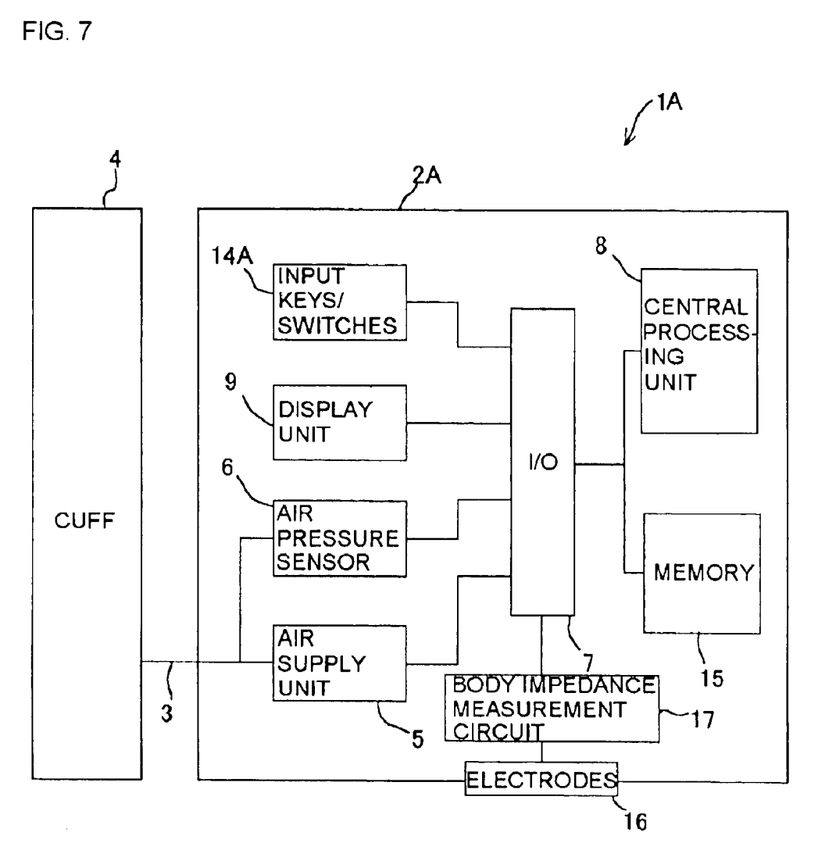
FIG. 7 is a block diagram of the visceral fat scale equipped with a sphygmomanometer according to the second embodiment.

FIGS. 6 and 7 show a general perspective view and block diagram, respectively, of a visceral fat scale equipped with a sphygmomanometer according to a second embodiment of the invention.

The visceral fat scale equipped with a sphygmomanometer 1A of the second embodiment has the function of measuring body impedance to obtain the percent body fat of the subject in addition to the same function as that of the visceral fat scale equipped with a sphygmomanometer 1 of the first embodiment. The parts identical to those of the first embodiment are indicated with the same reference numerals as in the first embodiment and a detailed explanation of them will be omitted herein.

The visceral fat scale equipped with a sphygmomanometer 1A of the second embodiment has electrodes 16 which are positioned at the front and back faces of the upper right and upper left ends of a machine body 2A and the fingers (e.g., a thumb and an index finger) of both hands of the subject touch the electrodes 16. By pinching each electrode 16 with the fingers of each hand, the body impedance between the fingers of the hand is measured by a body impedance measuring circuit 17, and the measurement data is input to the central processing unit 8 through the I/O circuit 7 and stored in the memory 15. Based on the measurement data, percent body fat is calculated. On the upper face of the machine body 2A, a percent body fat measurement starting switch 18 is provided in addition to the same input keys/switches as in the first embodiment. Herein, each electrode 16 is comprised of, for instance, an electrode for measurement disposed on the front face of the machine body 2A and an electrode for current application disposed on the back face of the same. Reference numeral 19 of FIG. 6 designates a stand for setting the machine body 2A up.

Figure 8:
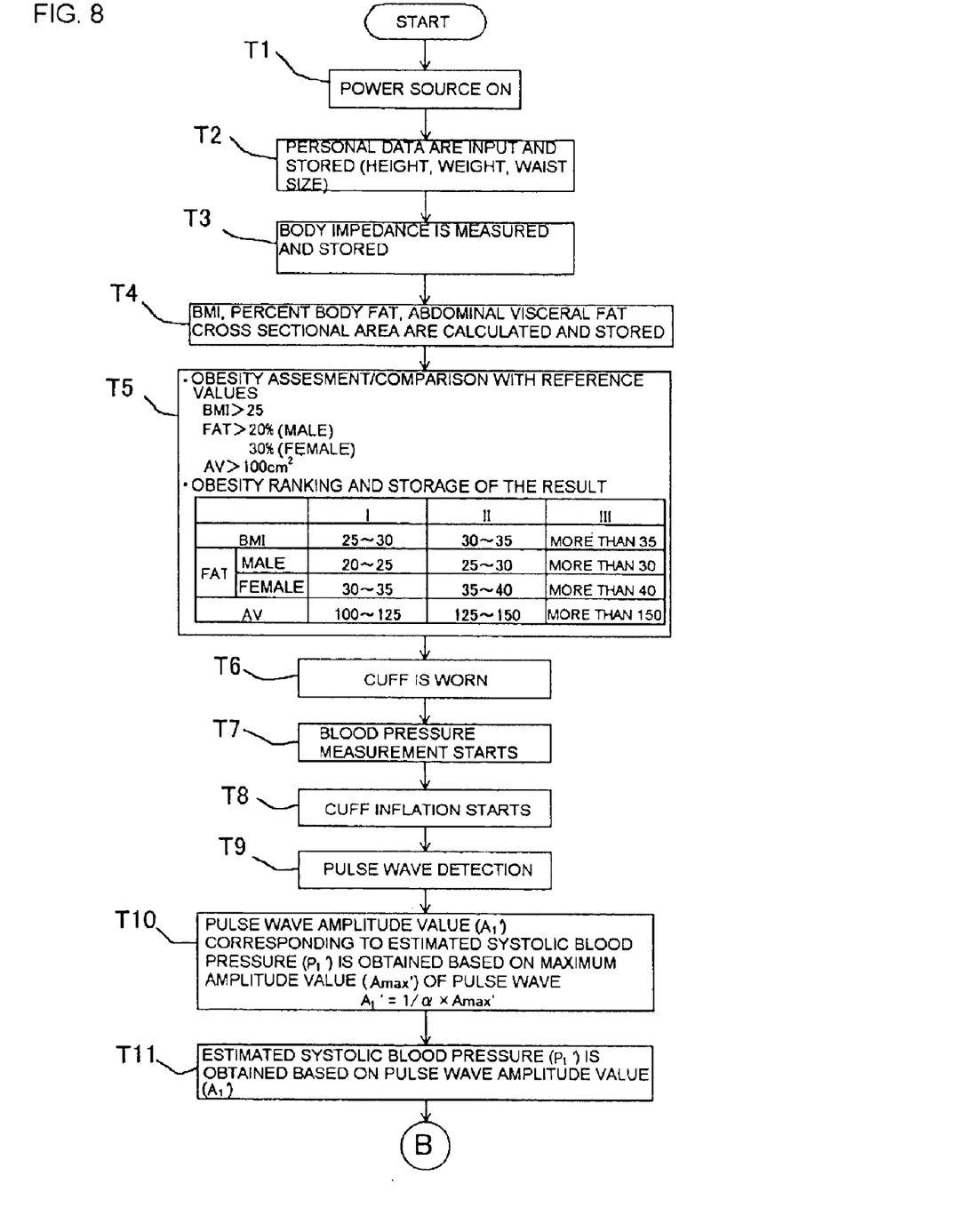
FIG. 8 is a flow chart (the first stage) of the operation of the visceral fat scale equipped with a sphygmomanometer according to the second embodiment.
Figure 9:
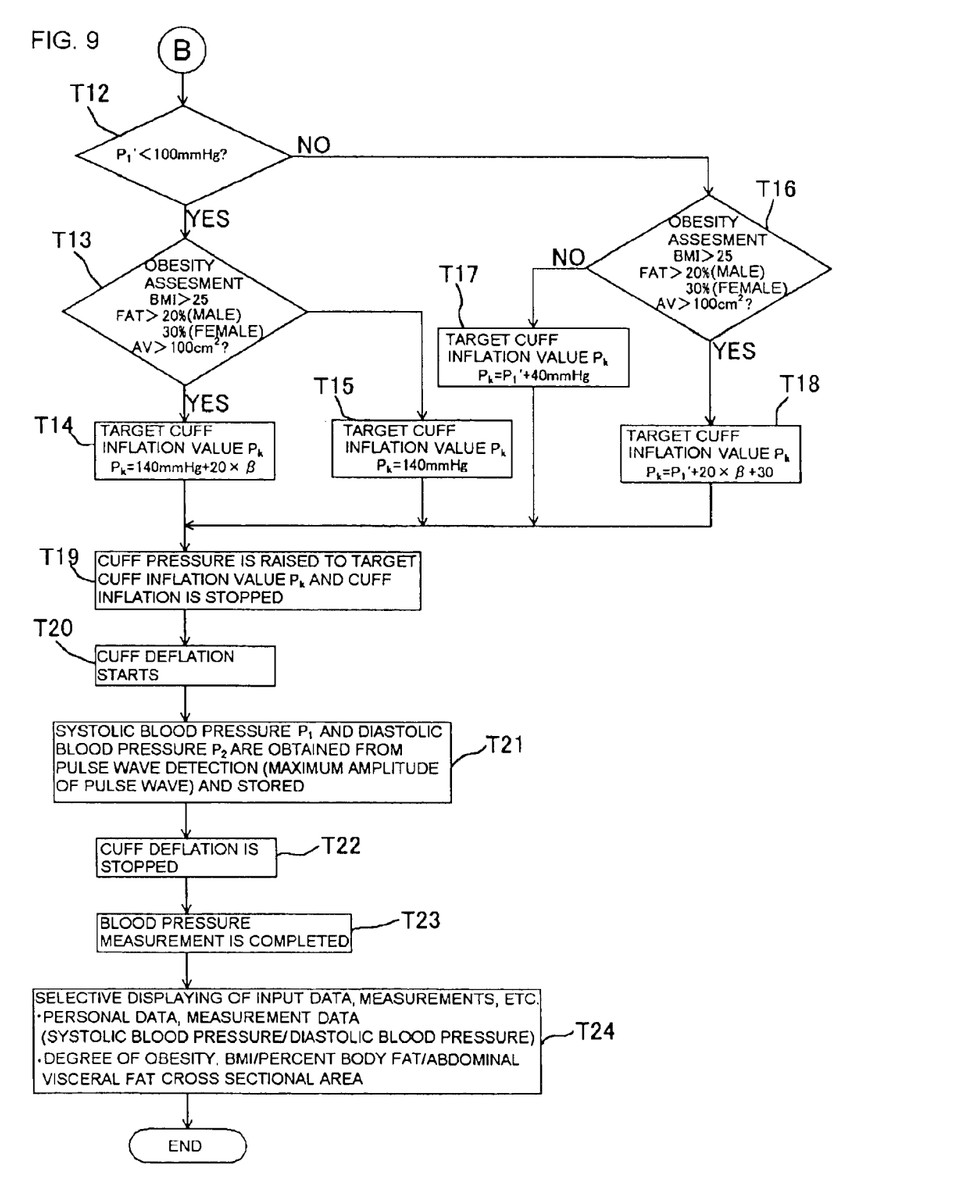
FIG. 9 is a flow chart (the second stage) of the operation of the visceral fat scale equipped with a sphygmomanometer according to the second embodiment.

Next, the operation of the visceral fat scale equipped with a sphygmomanometer 1A of the second embodiment will be described with reference to the flow charts of FIGS. 8 and 9. It should be noted that code T stands for a step.

T1: The power switch 10 is turned ON to put the machine body 2 into operation.

T2: By depressing the display mode selector key 13 and the increment/decrement key 12, the personal data of the subject such as height, weight, sex and waist size is selectively input. The data thus input is stored in the memory 15.

T3: After the percent body fat measurement starting switch 18 has been turned ON thereby making the scale ready for percent body fat measurement, the fingers of both hands are brought into contact with the electrodes 16 to measure the body impedance between the fingers of both hands and the measurement data is stored in the memory 15.

T4: The percent body fat of the subject is calculated based on the measurement data on the body impedance and the personal data stored in the memory 15, and the result of the calculation is stored in the memory 15. In the central processing unit 8, the BMI of the subject is calculated based on the personal data while performing calculation of the abdominal visceral fat cross-sectional area (AV) of the subject based on the personal data and the data on the body impedance or percent body fat. The results of the calculations are stored in the memory 15. The arithmetic expressions used for the above calculations have been stored in the memory 15 beforehand and are called into the central processing unit 8 when executing the arithmetic operations. As the expression for obtaining abdominal visceral fat cross-sectional area (AV), the following regression equation (9) is used, which is obtained by adding the auxiliary term of body impedance (Z) to the expression (1) used in the first embodiment:

$$AV = a_2 \times W_L + b_2 \times Z + d_2 \qquad (9)$$

where $W_L$ is waist size. The coefficients $a_2$, $b_2$ and constant $d_2$ of this expression are derived from a statistic technique based on the correlation between the waist size and abdominal cross-section C/T data of a selected group of subjects.

Instead of the regression expression (9), the following regression expression (10) may be used which is obtained by adding percent body fat (FAT) as an auxiliary term.

$$AV = a_3 \times W_L + c_1 \times FAT + d_3 \qquad (10)$$

The coefficients $a_3$, $c_1$ and constant $d_3$ of this expression are also derived from a statistic technique based on the correlation between the waist size and abdominal cross-section C/T data of a selected group of subjects.

Further, the following expression (11) may be used which provides a higher coefficient of correlation (r=0.9 or more) for the C/T data:

$$AV = e_1 \times W_L^2 \times H_L \times FAT + f_1 \times W_L^2 \times H_L \times Age + d_4 \qquad (11)$$

where $H_L$ is height and Age is age. The coefficients $e_1$, $f_1$ and the constant $d_4$ are derived from a statistic technique based on the correlation between the abdominal cross-section C/T data and values I, II of a selected group of subjects. Herein, the value I is obtained by multiplying the square of waist size by height and percent body fat, whereas the value II is obtained by multiplying the square of waist size by height and age.

Alternatively, the following equation (12) may be used:

$$AV = f_2 \times W_L^2 \times H_L \times Age + g_1 \times FAT + d_5 \qquad (12)$$

The coefficients $f_2$, $g_1$ and constant $d_5$ of this equation are derived from a statistic technique based on the correlation between the abdominal cross-section C/T data, percent body fat, and a value of a selected group of subjects, the value being obtained by multiplying the square of waist size by height and age.

T5: The BMI, percent body fat and abdominal visceral fat cross-sectional area (AV), which have been calculated at step T4 and stored in the memory 15, are compared to their respective reference values used for the obesity assessment and the rank of obesity is determined to be stored in the memory 15. The reference values and equation used for the above comparative operations have been stored in the memory 15 and called into the central processing unit 8 when executing the arithmetic operations.

As the reference values for the assessment of obesity, BMI=25 (for male and female), percent body fat (male: 20%, female: 30%), and abdominal visceral fat cross-sectional area (AV)=100 cm$^2$ (for male and female) are used. It should be noted that BMI is an index internationally used for assessment of obesity/emaciation, whereas abdominal visceral fat cross-sectional area (AV) represents the amount of distributed visceral fat and is used as an index to diagnosis of obesity in the clinical site. Obesity is ranked according to the indices BMI, percent body fat and AV. More specifically, BMI is classified as follows: the range of 25 to 30 is rank I, the range of 30 to 35 is rank II and the range of 35 or more is rank III. Percent body fat is classified as follows: for male, the range of 20 to 25% is rank I, the range of 25 to 30% is rank II and the range of more than 30% is rank III, and for female, the range of 30 to 35% is rank I, the range of 35 to 40% is rank II, and the range of more than 40% is rank III. Abdominal visceral fat cross-sectional area (AV) is classified as follows: the range of 100 to 125 cm$^2$ is rank I, the range of 125 to 150 cm$^2$ is rank II and the range of 150 cm$^2$ or more is rank III.

The steps T6 to T24 to be performed onward are basically the same as the steps S5 to S23 of the first embodiment except the following points: The steps T13 and T16 differ from the steps S12 and S15 of the first embodiment in that a check is made at the steps T13 and T16 whether or not percent body fat (FAT) exceeds 20% (in the case of male) or 30% (in the case of female). The step T24 differs from the step S23 of the first embodiment in that the display contents of the display unit 9 at the step T24 includes percent body fat as an index to the assessment of obesity. In view of this, a detailed description of the steps T6 to T24 will be omitted herein.

In the foregoing embodiments, the abdominal visceral fat cross-sectional area of the subject is obtained from the input personal data of the subject (height, weight, age, sex, waist size etc.), using an arithmetic expression stored beforehand. Herein, waist size may be estimated from the input data on the height, weight and age of the subject. An example of the equation used for this estimation is the following equation (13):

$$W_L = m_1 \times W/H_L^2 \times n_1 \times Age + 1_1 \qquad (13)$$

where W is weight, $H_L$ is height, and Age is age.

Based on the waist size which has been obtained from the above arithmetic operation and the personal data (height, weight, age, sex etc.) of the subject, the abdominal visceral fat cross-sectional area of the subject may be calculated with the arithmetic expression used in the foregoing embodiments. This saves the trouble of measurement and inputting of waist size, so that visceral fat can be more readily obtained.

What is claimed is:

1. A visceral fat scale equipped with a sphygmomanometer comprising a cuff, wherein after exerting the cuff exerts pressure to an artery of a subject by inflation of the cuff, the sphygmomanometer obtains the blood pressure of the subject based on a detected pulse wave signal, and the visceral fat scale comprising:
   an input device for inputting personal data of the subject;
   an arithmetic operation unit for calculating the amount of visceral fat of the subject based on the data input by the input device, the amount of visceral fat being the cross-sectional area of abdominal visceral fat of the subject; and
   a display unit for displaying a result of the calculation performed by the arithmetic operation unit.

2. The visceral fat scale equipped with a sphygmomanometer according to claim 1, wherein the personal data input by the input device includes the height, weight and waist size of the subject and wherein the arithmetic operation unit calculates the body mass index (BMI) of the subject in addition to the amount of visceral fat of the subject based on the data input by the input device.

3. The visceral fat scale equipped with a sphygmomanometer according to claim 2, wherein the display unit displays the respective ranks of the visceral fat amount and BMI of the subject, each of said indices having a plurality of ranks.

4. The visceral fat scale equipped with a sphygmomanometer according to claim 2 or 3, wherein the arithmetic operation unit makes an assessment of obesity by comparing the amount of visceral fat and BMI of the subject with their respective reference values for assessment which have been input beforehand, and wherein the display unit displays a result of the assessment of obesity.

5. The visceral fat scale equipped with a sphygmomanometer according to claim 1, wherein the display unit displays blood pressure values and the amount of visceral fat at the same time.

6. The visceral fat scale equipped with a sphygmomanometer according to claim 1, wherein the arithmetic operation unit calculates the amount of change from a previous measurement result and the ratio of the present measurement result to the previous measurement result for blood pressure values and visceral fat amount of the subject, and wherein the display unit displays a result of the amount of change and ratio calculation.

7. The visceral fat scale equipped with a sphygmomanometer according to claim 1, wherein a target inflation value for the cuff is determined by a systolic blood pressure estimated based on a pulse wave generated during cuff inflation and by a result of the assessment of obesity.

8. The visceral fat scale equipped with a sphygmomanometer according to claim 1, wherein a target inflation value for the cuff is determined by a systolic blood pressure estimated based on a pulse wave generated during cuff inflation and by the cross-sectional area of abdominal visceral fat.

9. A visceral fat scale equipped with a sphygmomanometer comprising a cuff, wherein, after the cuff exerts pressure to an artery of a subject by inflation of the cuff, the sphygmomanometer obtains the blood pressure of the subject based on a detected pulse wave signal, and the visceral fat scale comprising:
   an input device for inputting personal data including the height, weight and waist size of the subject;
   electrodes for current application and electrodes for measurement which are brought into contact with part of the body of the subject;
   a body impedance measuring unit for measuring the body impedance of the subject based on a signal from the measurement electrodes;
   an arithmetic operation unit for calculating at least any of the body mass index (BMI), percent body fat and visceral fat amount of the subject based on data input by the body impedance measuring unit and data input by the input device, said visceral fat amount being the cross-sectional area of abdominal visceral fat of the subject; and
   a display unit for displaying a result of the calculation performed by the arithmetic operation unit.

10. The visceral fat scale equipped with a sphygmomanometer according to claim 9, wherein a target inflation value for the cuff is determined by a systolic blood pressure estimated based on a pulse wave generated during cuff inflation and by the cross-sectional area of abdominal visceral fat.

11. The visceral fat scale equipped with a sphygmomanometer according to claim 9, wherein the display unit displays the rank of any of the BMI, percent body fat and visceral fat amount of the subject, each of said indices having a plurality of ranks.

12. The visceral fat scale equipped with a sphygmomanometer according to claim 9 or 11, wherein the arithmetic operation unit makes an assessment of obesity by comparing any of the BMI, percent body fat and visceral fat amount of the subject with their respective reference values for assessment which have been input beforehand, and wherein the display unit displays a result of the assessment of obesity.

13. The visceral fat scale equipped with a sphygmomanometer according to claim 9, wherein the display unit displays blood pressure values and the amount of visceral fat at the same time.

14. The visceral fat scale equipped with a sphygmomanometer according to claim 9, wherein the arithmetic operation unit calculates the amount of change from a previous measurement result and the ratio of the present measurement result to the previous measurement result for blood pressure values and visceral fat amount of the subject, and wherein the display unit displays a result of amount of change ratio calculation.

15. The visceral fat scale equipped with a sphygmomanometer according to claim 9, wherein a target inflation value for the cuff is determined by a systolic blood pressure estimated based on a pulse wave generated during cuff inflation and by a result of the assessment of obesity.

* * * * *

UNITED STATES PATENT AND TRADEMARK OFFICE
CERTIFICATE OF CORRECTION

PATENT NO. : 6,905,464 B2
DATED : June 14, 2005
INVENTOR(S) : Kawanishi et al.

It is certified that error appears in the above-identified patent and that said Letters Patent is hereby corrected as shown below:

Title page,
Item [54], Title, change "VISCERAL FAT METER PROVIDED WITH TONOMETER" to be -- VISCERAL FAT SCALE EQUIPPED WITH SPHYGMOMANOMETER --.

Signed and Sealed this

Twenty-second Day of November, 2005

JON W. DUDAS
*Director of the United States Patent and Trademark Office*